(12) United States Patent
Carr et al.

(10) Patent No.: US 7,739,903 B2
(45) Date of Patent: Jun. 22, 2010

(54) WEAK REFUEL DETECTION SYSTEM AND METHOD FOR VIRTUAL FLEX FUEL SENSOR SYSTEM

(75) Inventors: Mark D. Carr, Fenton, MI (US); Frank W. Schipperijn, Rochester, MI (US); Shuanita Robinson, Romulus, MI (US)

(73) Assignee: GM Global Technology Operations, Inc.

( * ) Notice: Subject to any disclaimer, the term of this patent is extended or adjusted under 35 U.S.C. 154(b) by 210 days.

(21) Appl. No.: 11/954,800

(22) Filed: Dec. 12, 2007

(65) Prior Publication Data

US 2009/0056430 A1 Mar. 5, 2009

Related U.S. Application Data

(60) Provisional application No. 60/969,297, filed on Aug. 31, 2007.

(51) Int. Cl.
*G01M 19/00* (2006.01)

(52) U.S. Cl. ............... 73/114.55; 73/114.38; 73/114.52

(58) Field of Classification Search .............. 73/114.38, 73/114.52, 114.53, 114.55, 114.56
See application file for complete search history.

(56) References Cited

U.S. PATENT DOCUMENTS

| | | | | |
|---|---|---|---|---|
| 5,881,703 | A * | 3/1999 | Nankee et al. | 123/686 |
| 5,901,671 | A * | 5/1999 | Huff et al. | 123/1 A |
| 6,041,278 | A * | 3/2000 | Kennie et al. | 701/103 |
| 6,257,174 | B1 * | 7/2001 | Huff et al. | 123/1 A |
| 7,159,623 | B1 | 1/2007 | Carr et al. | |
| 2008/0283030 | A1* | 11/2008 | Miersch-Wiemers et al. | 123/679 |

* cited by examiner

*Primary Examiner*—Eric S McCall

(57) ABSTRACT

The present disclosure, in one implementation, is directed to a method of estimating composition of fuel in the fuel tank of a vehicle. A refuel event is detected. A determination is made whether a volume of fuel added to the fuel tank satisfies a first threshold. A fuel composition estimation is suspended if the refuel event satisfies the first threshold. A total volume of fuel is accumulated based on a plurality of refuel events satisfying the first threshold. A new fuel composition is estimated based on the accumulated total volume of fuel satisfying a second threshold.

14 Claims, 4 Drawing Sheets

WEAK REFUEL DETECTION SYSTEM AND METHOD FOR VIRTUAL FLEX FUEL SENSOR SYSTEM

CROSS-REFERENCE TO RELATED APPLICATIONS

This application claims the benefit of U.S. Provisional Application No. 60/969,297, filed on Aug. 31, 2007. The disclosure of the above application is incorporated herein by reference.

FIELD

The present disclosure relates generally to vehicle fuel control, and more particularly to a system and method for estimating fuel composition in a vehicle fuel tank.

BACKGROUND

Closed loop fuel control systems are commonly used in gasoline-powered vehicles to maintain an operating air-fuel (A/F) ratio at stoichiometry. Stoichiometric values, however, can vary with fuel composition. For example, when fuel is added to a vehicle fuel tank, it mixes with fuel already in the tank. For example, ethanol or gasohol in varying mixtures can be added to gasoline already in the tank. If the added fuel has a different composition from that of the fuel already in the tank, the engine of the vehicle may need to operate at a different stoichiometric value after the refueling. Currently manufactured vehicles may include a hardware sensor that senses and communicates ethanol content in fuel to other systems in the vehicle.

SUMMARY

The present disclosure, in one implementation, is directed to a method of estimating composition of fuel in the fuel tank of a vehicle. A refuel event is detected. A determination is made whether a volume of fuel added to the fuel tank satisfies a first threshold. A fuel composition estimation is suspended if the refuel event satisfies the first threshold. A total volume of fuel is accumulated based on a plurality of refuel events satisfying the first threshold. A new fuel composition is estimated based on the accumulated total volume of fuel satisfying a second threshold.

According to other implementations, a fuel volume change is calculated. A percent change in fuel volume is calculated. The refuel event is determined based on the calculated fuel volume change, the percent change in fuel volume and the accumulated total weak volume of fuel.

Further areas of applicability of the present disclosure will become apparent from the detailed description provided hereinafter. It should be understood that the detailed description and specific examples, while indicating exemplary embodiments of the disclosure, are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION OF EXEMPLARY EMBODIMENTS

Figure 1:
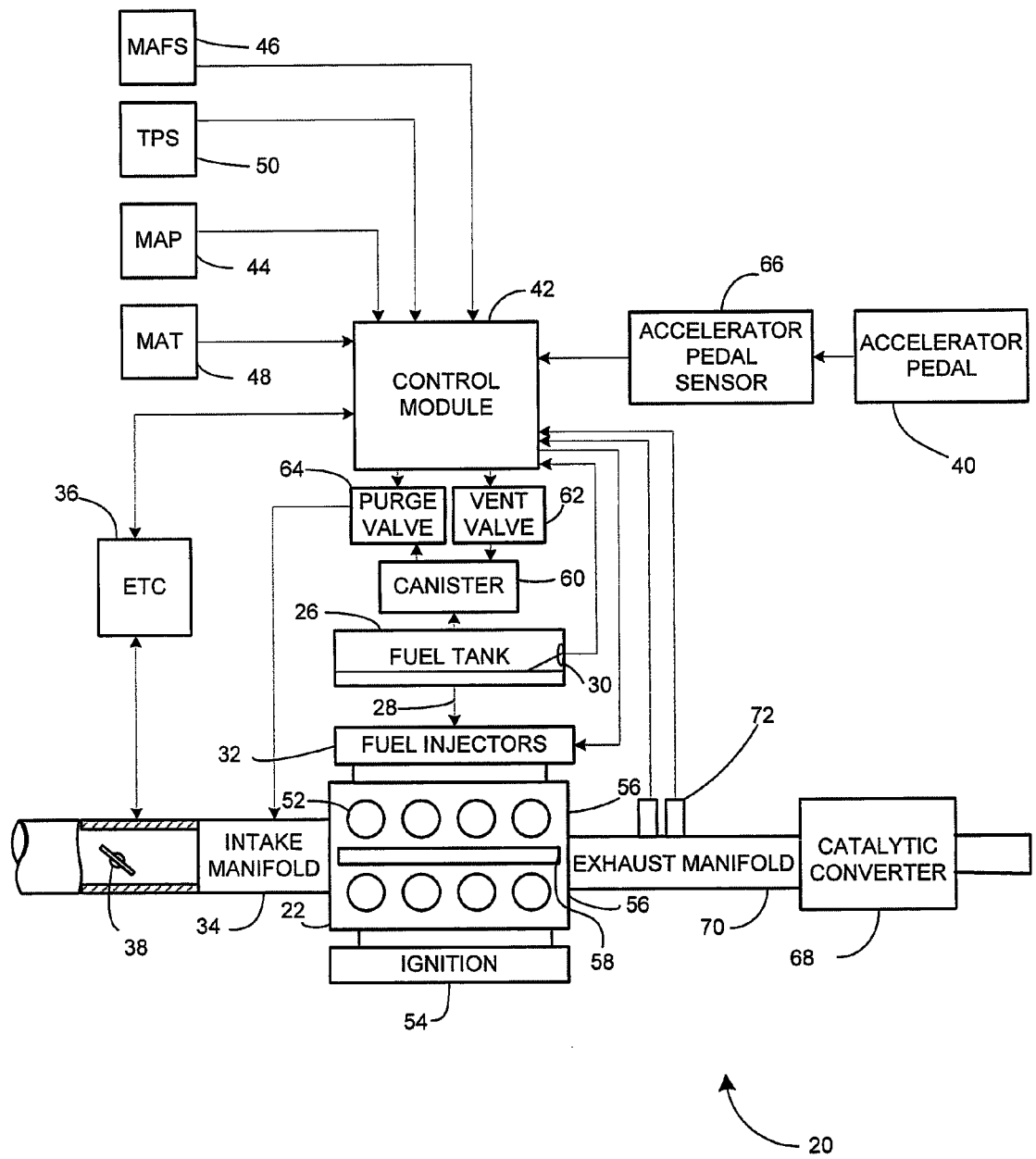
FIG. 1 is a functional block diagram of a vehicle including a fuel composition estimation system that detects weak refuel events in accordance with one implementation of the present disclosure.

The following description of various embodiments of the present disclosure is merely exemplary in nature and is in no way intended to limit the disclosure, its application, or uses. For purposes of clarity, the same reference numbers will be used in the drawings to identify similar elements. As used herein, the term module and/or device refers to an application specific integrated circuit (ASIC), an electronic circuit, a processor (shared, dedicated, or group) and memory that execute one or more software or firmware programs, a combinational logic circuit, and/or other suitable components that provide the described functionality.

The present disclosure, in one implementation, is directed to a method of estimating fuel composition, e.g., relative amounts of ethanol and gasoline, in a vehicle fuel tank. Generally, when a vehicle is refueled, a transition between existing and new fuel compositions happens at a nominally fixed rate when measured as a function of fuel consumed. Changes in fuel composition thus can be distinguished from fuel system faults, which generally happen either suddenly or very slowly. A slow fuel system fault may arise, for example, because of component aging. It is unlikely that a fuel system fault, when measured relative to fuel consumed, would occur at exactly the same rate as a fuel transition. The present disclosure is further directed to a method of determining when a weak refuel event has occurred. A weak refuel event generally can be a refuel event resulting in a volume of fuel being added to the vehicle fuel tank that has a volume less than a threshold. The threshold can correspond to any suitable volume of fuel such as two gallons for example. The method can suspend a fuel composition estimation when a weak refuel event has been detected. The method also can sum a series of weak refuel events. When the summed volume satisfies a threshold, a fuel composition can be determined.

Referring now to FIG. 1, a vehicle including a fuel composition estimation system that detects weak refuel events in accordance with one embodiment of the present disclosure is indicated generally by reference number 20. The vehicle 20 may be fueled with gasoline and/or ethanol in various percentages. Fuels appropriate for the vehicle 20 include but are not limited to gasoline, E85 (an alcohol fuel mixture that typically contains a mixture of up to 85% denatured fuel ethanol and gasoline or other hydrocarbon by volume), and "gasohol", which may include 90 percent gasoline and 10 percent ethanol as known in the art. Fuel is delivered to an engine 22 from a fuel tank 26 through a fuel line 28 and through a plurality of fuel injectors 32. A fuel sensor 30 senses a level of fuel in the tank 26 and communicates the fuel level to a control module 42. Air is delivered to the engine 22 through an intake manifold 34.

An electronic throttle controller (ETC) 36 adjusts a throttle plate 38 that is located adjacent to an inlet of the intake manifold 34 based upon a position of an accelerator pedal 40 and a throttle control algorithm that is executed by the control module 42. In controlling operation of the vehicle 20, the control module 42 may use a sensor signal 44 indicating pressure in the intake manifold 34. The control module 42 also may use a sensor signal 46 indicating mass air flow entering the intake manifold 34 past the throttle plate 38, a signal 48 indicating air temperature in the intake manifold 34, and a throttle position sensor signal 50 indicating an amount of opening of the throttle plate 38.

The engine 22 includes a plurality of cylinders 52 arranged in one or more cylinder banks 56. The cylinders 52 receive fuel from the fuel injectors 32 where it undergoes combustion in order to drive a crankshaft 58. Vapor from the fuel tank 26 can be collected in a charcoal storage canister 60. The canister 60 may be vented to air through a vent valve 62. The canister 60 may be purged through a purge valve 64. When vapor is purged from the canister 60, it is delivered to the intake manifold 34 and burned in the engine cylinders 52. The control module 42 controls operation of the vent valve 62, purge valve 64, fuel injectors 32 and ignition system 54. The control module 42 also is connected with an accelerator pedal sensor 66 that senses a position of the accelerator pedal 40 and sends a signal representative of the pedal position to the control module 42.

A catalytic converter 68 receives exhaust from the engine 22 through an exhaust manifold 70. Each of a pair of exhaust sensors 72, e.g., oxygen sensors, is associated with a corresponding cylinder bank 56. The oxygen sensors 72 sense exhaust in the manifold 70 and deliver signals to the control module 42 indicative of whether the exhaust is lean or rich. The signal output of the oxygen sensors 72 is used by the control module 42 as feedback in a closed-loop manner to regulate fuel delivery to each cylinder bank 56, e.g., via fuel injectors 32. It should be noted that configurations of the present disclosure are also contemplated for use in relation to vehicles having a single bank of cylinders and/or a single exhaust manifold oxygen sensor.

In some implementations, the sensors 72 are switch-type oxygen sensors as known in the art. The control module 42 may use the sensor 72 feedback to drive an actual air-fuel ratio to a desired value, usually around a stoichiometric value. A plurality of predefined engine operating regions are referred to by the control module 42 in controlling fuel delivery to the engine 22. Operating regions may be defined, for example, based on speed and/or load of the engine 22. The control module 42 may perform control functions that vary dependent on which operating region of the vehicle is currently active.

Fuel, air and/or re-circulated exhaust to the engine 22 may be adjusted, i.e., trimmed, to correct for deviations from a desired air-fuel ratio. Trim values used to make such corrections may be stored in control module 42 memory locations corresponding to a plurality of predefined closed loop air-fuel ratio control cells (also referred to as sub-regions) associated with the operating regions of the vehicle 20. Cell values are used to provide closed-loop fuel, air and/or re-circulated exhaust control. For example, long-term multipliers (LTMs) may be used to provide long-term corrections to fuel commands to the engine 22 in response to changing engine conditions. LTMs typically are stored in a memory lookup table in non-volatile memory. The control module 42 adjusts LTMs periodically in accordance with a long-term time period, e.g., using a period that is longer than 1 second such as ten seconds. Such adjustment may be referred to as "long-term learning".

Additionally or alternatively, short-term integrators (STIs) may be used to provide short-term corrections to fuel commands to the engine 22 in response to engine conditions. The control module 42 adjusts STIs periodically in accordance with a short-term time period, e.g., using a period that is less than one second such as every 6.25 milliseconds. Such adjustment may be referred to as "short-term learning". An STI may be stored in volatile memory and may be adjusted based on an active cell LTM and a signal of the oxygen sensor 72.

In accordance with one implementation of the present disclosure, the control module 42 maintains a fuel trim memory structure (such as a lookup table for example) for use in estimating fuel composition. A plurality of closed loop correction ("CLC") cells can be associated with each cylinder bank 56. For example, eight cells may be provided for each bank 56. CLC cells are defined based on mass air flow to the engine 22 and may be used to record a total closed-loop fuel trim of the engine 22 at various operating conditions. The control module 42 stores baseline closed loop correction values for the engine operating regions in the CLC cells. Baseline CLC values may be updated when purge is commanded off as further described below. The baseline CLC values provide a basis for determining new fuel/air estimates.

CLC cell values are stored in non-volatile memory. A CLC value is obtained by multiplying LTM and STI corrections for an active closed-loop fuel control cell. In other configurations, CLC values may be combined in other ways. For example, a CLC value may be obtained in another configuration by adding LTM and STI corrections for an active closed-loop fuel control cell. In the present configuration, the control module 42 uses separate structures for closed loop fuel control and for fuel composition estimation. The structures are separate so that the fuel composition estimation structure may remain current over ignition cycles, even though the closed loop fuel control structure might be reset upon vehicle system power-up. It should be noted generally that configurations also are contemplated in which a vehicle control module may use a single memory structure for both closed loop fuel control and fuel composition estimation. Further details of a control module that estimates fuel composition according to the present teachings may be found in commonly owned U.S. Pat. No. 7,159,623, the disclosure of which is incorporated by reference in its entirety.

Figure 2:
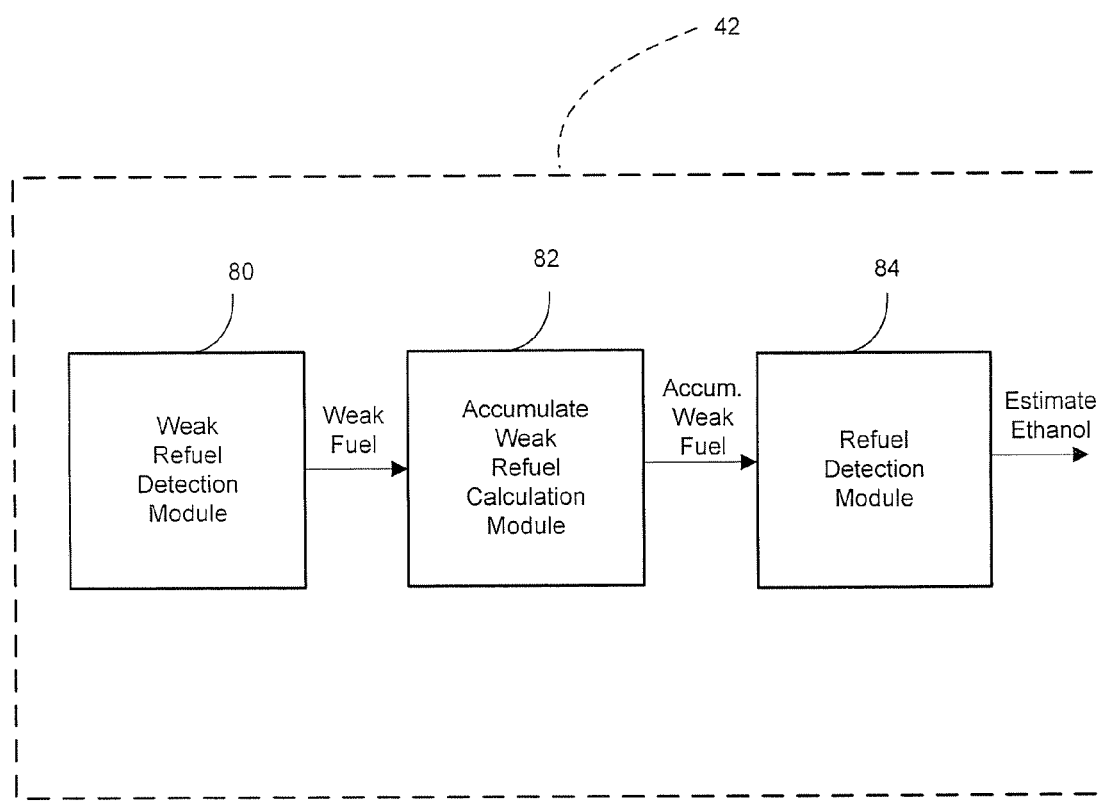
FIG. 2 is a functional block diagram of a control module in accordance with one implementation of the present disclosure.

In one implementation as depicted in FIG. 2, the control module 42 can include a weak refuel detection module 80, an accumulated weak refuel module 82 and a refuel detection module 84.

Figure 3:
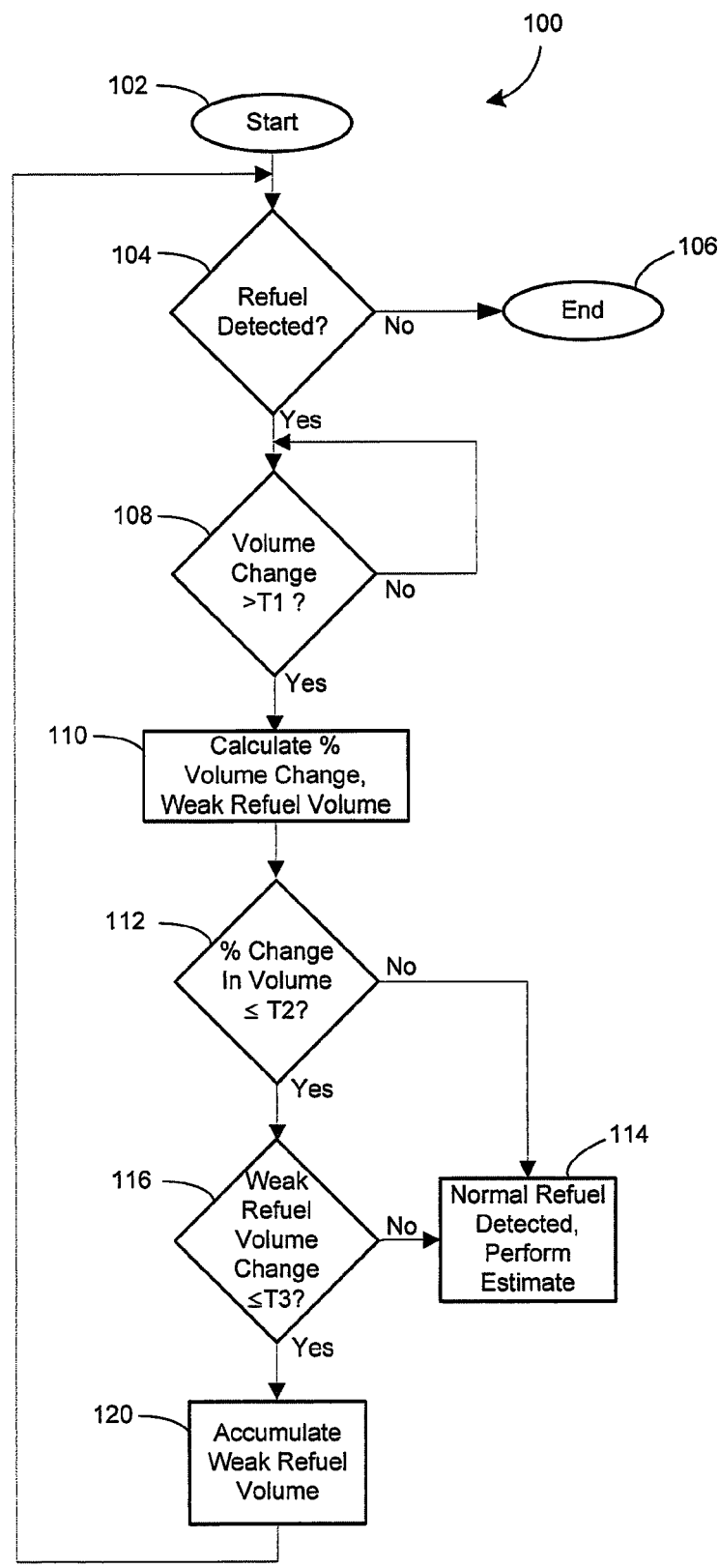
FIG. 3 is a flow diagram of a method of detecting a refuel event in accordance with one implementation of the present disclosure.

A flow diagram of one implantation of the refuel detection module 80 is indicated generally by reference number 100 in FIG. 3. Control begins in step 102. In step 104, control determines if a refuel event has been detected. In one example, a refuel event can be determined based on a fuel level communicated to the control module 42 from the fuel sensor 30. If a refuel event has been detected, control determines whether a change in fuel volume is greater than a threshold T1 in step 108. If a refuel event is not detected, control ends in step 106. If the change in fuel volume is greater than T1, control determines if a percent change in fuel volume is less than or equal to a threshold T2 in step 112. If the fuel volume is not greater than T1, control loops to step 108. If the fuel volume is greater than T1, control calculates a percent of fuel volume change and a weak refuel volume in step 110.

If the percent change in fuel volume is less than or equal to T2 in step 112, control determines if a weak refuel volume change is less than or equal to T3 in step 116. If the percent change in fuel volume not less than or equal to T2 in step 112, control assumes a normal refuel event has occurred and performs a fuel composition (ethanol concentration) estimation in step 114. If the weak refuel volume change is less than or equal to T3 in step 116, control accumulates a weak refuel volume in step 120. If the weak refuel volume change is not less than or equal to T3 in step 116, control assumes a normal refuel event has occurred and performs a fuel composition estimate in step 114.

Figure 4:
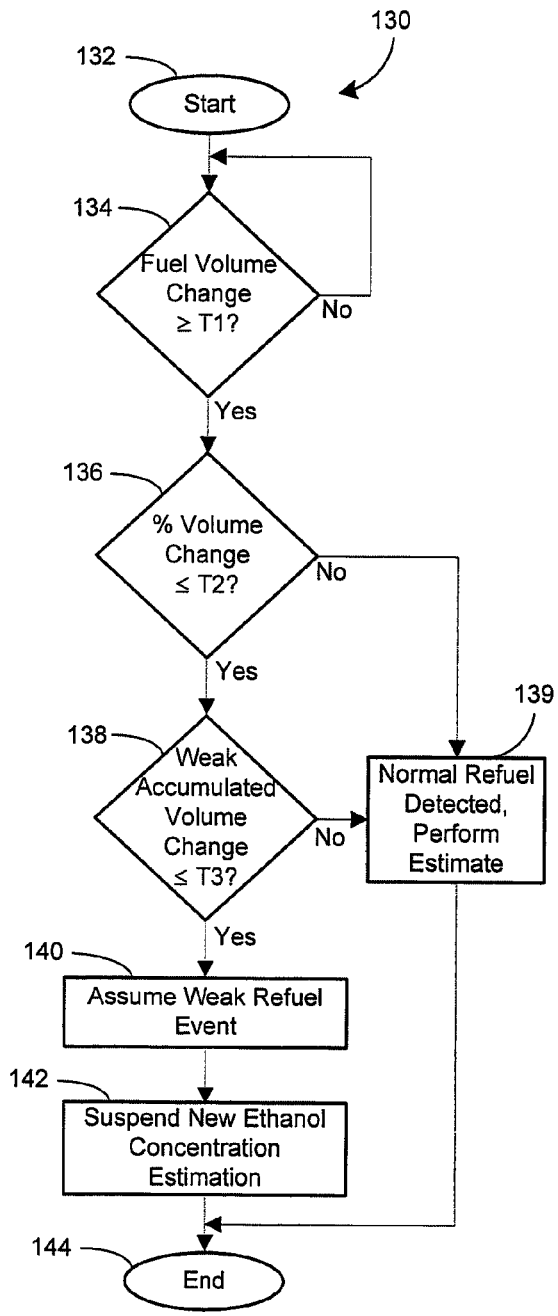
FIG. 4 is a flow diagram of a method of detecting a weak refuel event in accordance with one implementation of the present disclosure.
Figure 5:
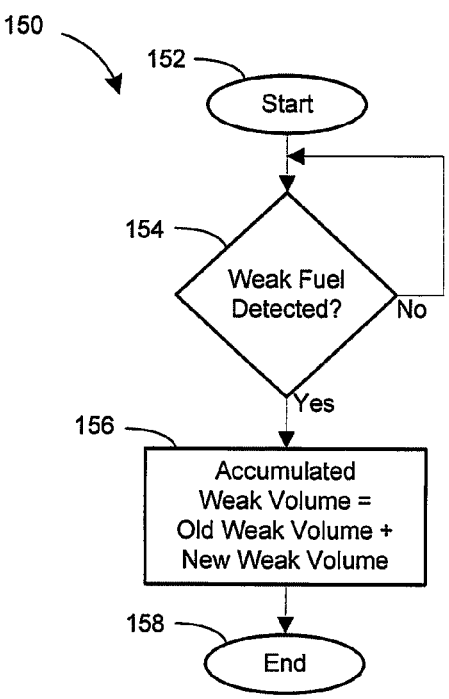
FIG. 5 is a flow diagram of a method of calculating an accumulated weak fuel volume in accordance with one implementation of the present disclosure.

The weak refuel detection module 80 will now be described. In general, the weak refuel detection module 80 determines if a small volume of fuel has been added to the fuel tank 26. A flow diagram of one implementation of the weak refuel detection module 80 is indicated generally by reference number 130 in FIG. 4. Control starts in step 132. The change in fuel volume is compared to the threshold T1 in step 134. If the change in fuel volume is greater than or equal to the threshold T1, control determines whether a percent change of fuel volume is less than or equal to the threshold T2 in step 136. If not, control loops to step 134. If the percent change of fuel volume is less than or equal to the threshold T2, control determines whether a weak accumulated volume change (described later in FIG. 5) is less than or equal to the threshold T3 in step 138. If the percent change of fuel volume is not less than or equal to the threshold T2, control assumes a normal refuel event has occurred and performs a fuel composition estimate in step 139 and loops to step 144. If the weak accumulated volume change is less than or equal to the threshold T3, control assumes a weak refuel event has occurred in step 140. If not, control proceeds to step 139. Control suspends new ethanol concentration estimation in step 142. Control ends in step 144.

The accumulated weak fuel calculation module 82 will now be described. In general, the accumulated weak fuel calculation module 82 sums sequential volumes of fuel satisfying a weak refuel criteria. A flow diagram of one implementation of the accumulated weak fuel calculation module 82 is indicated generally by reference number 150 in FIG. 5. Control starts in step 152. In step 154, control determines if a weak refuel has been detected. If a weak refuel has been detected, control sets an accumulated weak fuel volume equal to an old weak volume plus the new weak fuel volume in step 156. If a weak refuel event is not detected in step 154, control loops to step 154. Control ends in step 158.

Implementations of the foregoing system and method make it possible to account for very small refuel events (such as less than two gallons) to estimate not only fuel composition with accuracy, but also to perform closed-loop fuel control, spark control, system diagnostics and other vehicle functions with increased accuracy.

Those skilled in the art can now appreciate from the foregoing description that the broad teachings of the present disclosure can be implemented in a variety of forms. Therefore, while this disclosure has been described in connection with particular examples thereof, the true scope of the disclosure should not be so limited since other modifications will become apparent to the skilled practitioner upon a study of the drawings, specification, and the following claims.

What is claimed is:

1. A method of estimating composition of fuel in the fuel tank of a vehicle, said method comprising:
   detecting a refuel event;
   determining if a volume of fuel added during said refuel event satisfies a first volume threshold;
   identifying a fuel volume that does not satisfy the first volume threshold as a weak fuel volume;
   continuing said detecting and determining until a total weak fuel volume summed from sequential refueling events having said weak fuel volume satisfies a second volume threshold; and
   estimating a fuel composition based on satisfying said second volume threshold.

2. The method of claim 1 wherein detecting said refuel event comprises determining a level of fuel in the fuel tank.

3. The method of claim 1 wherein estimating further comprises estimating a fuel composition based on satisfying said first volume threshold.

4. The method of claim 1 wherein said determining if said volume of fuel added comprises calculating a fuel volume change.

5. The method of claim 4 wherein determining if said volume of fuel added comprises calculating a percent change in fuel volume.

6. A system for estimating composition of fuel in the fuel tank of a vehicle, the system comprising:
   a weak fuel detection module that determines if a volume of fuel added during a refuel event satisfies a first volume threshold;
   an accumulated weak fuel calculation module that accumulates a total volume of fuel based on a plurality of refuel events that are each too small to satisfy said first volume threshold; and
   a refuel detection module that estimates a fuel composition based on said total volume of fuel satisfying a second volume threshold.

7. The system of claim 6 wherein said accumulated weak refuel calculation module sums a first volume of fuel that is too small to satisfy said first threshold with subsequent volumes of fuel that are each too small to satisfy said first threshold.

8. The system of claim 6 wherein said refuel detection module determines a level of fuel in the fuel tank.

9. The system of claim 6 wherein said refuel detection module estimates a fuel composition based on satisfying said first volume threshold.

10. The system of claim 6 wherein said weak fuel detection module calculates a fuel volume change.

11. The system of claim 10 wherein said weak fuel detection module calculates a percent change in fuel volume.

12. A method of estimating composition of fuel in the fuel tank of a vehicle, said method comprising:
   detecting a refuel event;
   determining fuel volume change in the fuel tank;
   determining a percent fuel volume change in the fuel tank;
   determining if said refuel event satisfies a first threshold based on said fuel volume change and said percent fuel volume change;
   identifying sequential volumes of fuel from sequential refueling events that are each too small to satisfy said first threshold;
   accumulating a total volume of fuel based on said sequential volumes of fuel that are each too small to satisfy said first threshold; and
   estimating a fuel composition based on said accumulated total volume of fuel satisfying a second threshold.

13. The method of claim 12 wherein detecting said refuel event comprises determining a level of fuel in the fuel tank.

14. The method of claim 12 wherein estimating further comprises estimating a fuel composition based on satisfying said first threshold.

* * * * *